United States Patent [19]

Frost et al.

[11] 4,022,806

[45] May 10, 1977

[54] PROCESS FOR PREPARING CHENODEOXYCHOLIC ACID

[75] Inventors: Henry Francis Frost, Hemel Hempstead; Fritz Fabian, Welwyn Garden City; Christopher James Sharpe, Harrow Weald; William Arthur Jones, Staines, all of England

[73] Assignee: The Union International Company Ltd., England

[22] Filed: Dec. 23, 1975

[21] Appl. No.: 643,902

[30] Foreign Application Priority Data

Dec. 23, 1974 United Kingdom ............ 55575/74

[52] U.S. Cl. ............................................ 260/397.1
[51] Int. Cl.$^2$ ........................................ C07J 9/00
[58] Field of Search ................................ 260/397.1

[56] References Cited

UNITED STATES PATENTS

| 3,833,620 | 9/1974 | Saltzman | 260/397.1 |
| 3,839,565 | 10/1974 | Saltzman | 424/238 |

Primary Examiner—Elbert L. Roberts

[57] ABSTRACT

A process for preparing a form of chenodeoxycholic acid having a melting point of ca. 166° C from the amorphous form of the acid or from the form melting at ca. 120° C. The amorphous or low melting forms of chenodeoxycholic acid, in a suspension in water, are seeded with preprepared crystalline acid of the high melting form and the acid product treated, in suspension, at a temperature of not greater than 85° C to complete the conversion of the chenodeoxycholic acid to the high melting form. Crude chenodeoxycholic acid of the low melting form is purified by a process which involves forming a mixture of the crude acid, methanol, a base and a calcium or strontium salt, separating the precipitated crystalline calcium or strontium chenodeoxycholanate, dissolving the salt in a solution of acetic or propionic acid, diluting the solution with water to precipitate the free acid in purified form and recovering the purified acid.

25 Claims, No Drawings

PROCESS FOR PREPARING CHENODEOXYCHOLIC ACID

U.S. Pat. No. 3,836,550 of common assignee herewith describes and claims a process for the purification of crude chenodeoxycholic acid which comprises forming a mixture of methanol, the crude acid, a base and a calcium or strontium salt, whereby the crystalline calcium or strontium salt of the chenodeoxycholic acid is precipitated, separating the salt, treating the separated salt with an acidic reagent and isolating purified chenodeoxycholic acid. In a preferred aspect, this involves combining crude chenodeoxycholic acid, calcium chloride and from 35 to 40 ml of methanol per gram of crude acid and rendering the mixture alkaline by the addition of ammonium hydroxide. This precipitates the crystalline calcium salt of the acid which is then separated, acidified and the purified acid extracted and recovered. Typically as exemplified in the specification, the calcium salt is acidified with hydrochloric acid and extracted with ethyl acetate. After washing the ethyl acetate extract with water and then drying the extract by, for example, treatment with a suitable chemical drying agent or by azeotropic distillation, the pure chenodeoxycholic acid is precipitated by the slow addition of petroleum ether. This solid product is filtered off and dried to give the final pure product.

The use of acids such as hydrochloric acid as the acidic reagent for producing the free chenodeoxycholic acid from the calcium or strontium salt of the acid is inconvenient, due to the fact that such acids in general give rise to insoluble products with the chenodeoxycholic acid salts, and the free acid is itself insoluble in these aqueous acid solutions. It is necessary therefore with these acids, to take up the chenodeoxycholic acid again in an organic solvent and where such a solvent (e.g. ethyl acetate) is present with the acid solutions, a two-phase system is produced which is inconvenient from the point of view of handling of the products. It has now been found that the functions of acidic reagent and solvent to dissolve the chenodeoxycholic acid product, can be combined if either acetic or propionic acid is used for this stage. The process is thereby greatly improved and simplified, the salt being conveniently taken up in acetic or propionic acid solution and the chenodeoxycholic acid so formed being very readily precipitated from the solution by the addition of water thereto, or conversely by pouring the chenodeoxycholic acid solution into water. The precipitated pure acid may then be separated and dried in the usual manner.

According to one aspect of the present invention therefore, a process for the purification of crude chenodeoxycholic acid is provided, which comprises forming a mixture of methanol, the crude acid, a base and a calcium or strontium salt, whereby the crystalline calcium or strontium salt of chenodeoxycholic acid is precipitated, separating the salt, dissolving it in a solution of acetic acid or propionic acid, diluting this solution with water to precipitate the free acid in purified form and recovering the purified chenodeoxycholic acid.

In this way chenodeoxycholic acid having a loss on drying (at 105° C for 2 hours) of less than 1% and an ash content of less than 0.1% is obtained.

It is preferred to use the acetic and propionic acids in aqueous solutions which are as dilute as possible, consistent with adequate solubility, since the higher the concentration of acid the greater is the extent of acylation of the chenodeoxycholic acid which occurs. Lower concentrations of acid can be used for the conversion of strontium chenodeoxycholate than for the calcium salt, as indicated by the following tests.

Using chenodeoxycholic acid prepared from cholic acid by the Wolff-Kishner route as outlined in U.S. Pat. No. 3,836,550 the calcium and strontium salts were prepared by a process as described in that patent. Portions of these were suspended, at a concentration of 0.2 g/ml, in dilute aqueous acetic or propionic acid and the suspensions heated in a bath at 50° C with occasional stirring, with the following results:

| Acid used (aq. v/v) | Calcium salt | Strontium salt |
|---|---|---|
| 60 % acetic acid | Completely soluble; no solid phase on cooling | Completely soluble; dissolved without heating |
| 50 % acetic acid | Solution incomplete | Solution incomplete |
| 50 % propionic acid | Completely soluble | Completely soluble |
| 40 % propionic acid | Soluble; solid phase formed on removal from bath. | Soluble; solid phase formed on removal from bath. |

Formic acid is a less effective solvent and although the salts had adequate solubility in aqueous formic acid at 80% ($v$/v), there was found to be, under these conditions, an unacceptable degree of formylation of the chenodeoxycholic acid.

In regard to another aspect of the purification process described in the parent specification, it is stated therein that in the case of using a calcium salt, the quantity of methanol required to give the optimum purification is from 35 to 40 ml/g. of crude chenodeoxycholic acid. It has now been found that this amount can be reduced to around 10 ml/g. of crude acid, provided that the crude material is not too highly contaminated by impurities. In this event, smaller amounts of methanol suffice to effect purification of the chenodeoxycholic acid through formation of the crystalline calcium salt of the acid.

The chenodeoxycholic acid produced by the process described in the parent patent and the improvements thereto described above is material having a melting point in the range of approximately 115° to 125° C. For example the melting point reported in the Merck Index (8th Edition, 1968) is 119° C for a product obtained from a mixture of ethyl acetate and heptane. This product is known to contain approximately 7% by weight of heptane as very tenaciously held solvent of crystallization (Mosbach, Nicolan and Nicholas, Lancet, July 1974, p. 11). Applicants have found that a material melting at approximately 120° C can in fact be obtained by crystallisation from ethylacetate alone, or from butanone. However in both cases solvent of crystallization is present and is difficult to remove by conventional drying methods. Three distinct forms of chenodeoxycholic acid are in fact now known, namely, two crystalline forms melting at ca. 120° C and ca. 166° C, and an amorphous form melting at ca. 142° C. Data obtained by differential thermal analysis and differential scanning calorimetry of the three forms substantiate that these are different physical forms.

The low melting form (as referred to throughout this specification) has two overlapping endotherms, the first of which (at 112° C) is probably due to loss of solvent of crystallisation, followed by another at 120° C indicating melting. The high melting form (as referred to herein) shows a sharp endotherm at 169° C, characteristic of true melting. On the other hand, the amorphous form (as referred to herein) gives a small endotherm at 132° related to loss of solvent, followed by a broad shallow endotherm centred at approximately 143°–144° C. The latter is consistent with a transition from a supercooled liquid.

The two crystalline forms in the powdered state are easily differentiated from the amorphous form by their appearance under a polarising microscope and further by their X-ray powder diffraction patterns. Infra-red spectra obtained on Nujol mulls of the three forms also serve to differentiate them. Conversely, they can be shown to be identical chemical species by dissolving each in methanol and applying the solutions to solid potassium bromide which is then dried, powdered and formed into discs under pressure and again obtaining their infra-red spectra. Under these conditions the spectra are identical (see G. A. D. Haselwood, "Bile Salts", Methuens, Monographs on Biochemical Subjects, 1967, p. 34).

The amorphous form of chenodeoxycholic acid may readily be obtained by dissolving the acid of melting point 115° to 125° C in alcohol and precipitating it from the alcohol solution by the addition of water, followed by rapidly drying the product.

It has now been found that the high-melting form of chenodeoxycholic acid (as herein defined) can be prepared by seeding an aqueous suspension of either the low-melting or amorphous forms of the acid, the seeding material being a small quantity of the crystalline high melting point form of the acid which may be prepared by the following methods.

Chenodeoxycholic acid (either in the low-melting or amorphous form) is dissolved in dilute sodium hydroxide and 2N hydrochloric acid added until the pH of the solution reaches approximately 1. The precipitate formed at this stage is collected on a sintered glass funnel, washed with water and placed in a vacuum oven at 75° and 50 torr. After 15 minutes drying the product becomes fused and after being broken up and further dried under the same conditions for about 2 hours, a dry powder product is obtained. This softens slightly at 130°, partially melts at 145° and completely at 162°.

To obtain small amounts of the higher melting point form of the acid in a more homogeneous state, a sample of the low melting or amorphous form of the acid was heated in a melting point tube to 150° C at a very slow heating rate such that melting of the material was avoided, and held at this temperature for from 5 to 10 minutes, again without melting occurring. This treated material was then used to seed a warm solution of chenodeoxycholic acid (of low melting or amorphous form) in acetonitrile in order to obtain further quantities of the higher melting form of the acid for seeding purposes. The melting point of this (crystalline) material was found to be 165°–166° C.

Using such material as the seeding agent the present invention according to another aspect thereof thus provides a process for transforming chenodeoxycholic acid wherein acid in the low-melting or amorphous forms (as herein defined) in aqueous suspension, is seeded with a sample of preprepared crystalline high-melting form of the acid (as herein defined) and finally treated at a temperature not greater than 85° C to convert it completely to material of the high melting form. Since crystallization of an organic material is to some extent affected by the purity of the material as is known, the difficulty attending such a process is dependent upon both the nature and quantity of the impurity present in the material. As a consequence, in order to carry out the present process effectively, the acid used as starting material must be of sufficient purity, and conveniently the starting material is a material produced by the process of U.S. Pat. No. 3,836,550 or produced according to the improved process which comprises one aspect of the present invention, as previously described. Most conveniently pure chenodeoxycholic acid of the high melting point form is produced by first preparing the crystalline calcium salt of chenodeoxycholic acid (in the low melting or amorphous form) according to the process of U.S. Pat. No. 3,836,550, taking up the crystalline calcium salt in aqueous acetic acid thereby to form a solution of the free chenodeoxycholic acid, precipitating the free acid by dilution with water, and seeding the suspension of free chenodeoxycholic acid in water so formed with pure chenodeoxycholic acid of high melting point form (as herein defined). To convert the product entirely to the high melting form, it is treated at a temperature not greater than 85° C, the treatment conveniently being by heating a suspension of the product in water to a temperature not greater than 85° C, or by subjecting such a suspension to ultrasonic vibration while maintaining the temperature at or below 85° C. In the latter way the solid chenodeoxycholic acid product is converted entirely to the higher melting form in about 15 minutes.

The seeding and subsequent heating steps of the process may conveniently be carried out by pouring the solution of the calcium salt in acetic acid into cold water in which is suspended a small quantity of the high melting material, separating the precipitated acid, washing the precipitate, suspending the precipitate again in water and warming the suspension slowly to a temperature which is not greater than 85° C.

Before the heating stage, i.e. after the initial precipitation, the material formed is a mixture of forms having an indefinite melting point between about 140° C and about 160° C and the heating or ultrasonication stage serves to convert the material entirely to the high melting form. Above 85° C, the material converts to a sticky mass, but to obtain a faster rate of conversion a relatively high temperature should be used, and a temperature in the range of 65° to 80° C is preferred, for this treatment step.

After treating to convert fully the chenodeoxycholic acid product to the high melting form, the acid is then filtered off and dried to give the final product.

The high melting point material has advantages over the usual chenodeoxycholic acid of low melting or amorphous form as it has better handling properties owing to its more granular character and higher bulk density. It is consequently also more easily formulated in therapeutic compositions to be used for the dissolution of gall stones in the treatment of cholelithiasis. Furthermore the high melting form is less prone to dimerise during heating, which is an advantage in relation to the drying of the product.

The preparation of purified chenodeoxycholic acid of high melting point is further illustrated by the following examples.

EXAMPLE 1

20 g of crystalline calcium chenodeoxycholanate (prepared according to the process of U.S. Pat. No.

3,836,550) was dissolved in 120 ml 60% acetic acid, with stirring and warming to 50° C. Complete solution occurred within 30 minutes. This solution was poured into 1 l of cold water in which about 0.2 gm. of high melting point seeding material was suspended. (In this case the seeding material was from a previous batch produced by seeding, but otherwise seed crystals can be used which are obtained ab initio as described previously). After intensive stirring the precipitated material was separated by filtration. Two washes were given to about 1 l. water each, using intensive stirring and filtration. After the second wash, the material was suspended again in 1 l. water and slowly heated with intensive stirring up to 80° C. During this heating process it was possible to follow clearly the change in the characteristics of the chenodeoxycholic acid: whilst the material was at first voluminous, at the end of the heating period it became very finely granular and settled rapidly. After cooling to 45° C the solids were separated by filtration and dried at 60° C and 80 torr vacuum for 16 hours. The yield was 93.5% and the melting point of the material (without any previous softening) was 163°–165° C. The purity of the product as determined by GLC against an internal standard was 99.6%.

EXAMPLE 2

20 g of crystalline calcium chenodeoxycholate (as in example 1) was dissolved in 120 ml of 60% propionic acid (v/v), with stirring and warming to 50° C. This solution was treated in the same way as the acetic acid solution of example 1, to obtain a similar product.

EXAMPLE 3

Amorphous chenodeoxycholic acid (0.1 g) and crystalline chenodeoxycholic acid (m.p. 164°–166° C, 0.01 g) were suspended in water (6 ml) and subjected to ultrasonication with an M.S.E. Ultrasonicator, model 150W, using a 3mm diameter microprobe, in a small beaker immersed in an ice bath. Full power was applied for three five-minute periods. The product was filtered off and dried at 70° C in a vacuum oven, giving 0.1 g crystalline material, m.p. 162°–166° C.

What is claimed is:

1. A process for the purification of crude chenodeoxycholic acid which comprises forming a mixture of methanol, the crude acid, a base and a calcium or strontium salt, whereby the crystalline calcium or strontium salt of chenodeoxycholic acid is precipitated, separating the salt, dissolving it in a solution of acetic acid or propionic acid, diluting this solution with water to precipitate the free acid in purified form and recovering the purified acid.

2. A process as claimed in claim 1, wherein a solution of acetic acid is used.

3. A process as claimed in claim 1, in which a solution of propionic acid is used.

4. A process as claimed in claim 2, in which the concentration of the acetic acid solution is about 60% v/v.

5. A process as claimed in claim 2, in which the concentration of the propionic acid solution is from about 40% to about 50% v/v.

6. A process as claimed in claim 1, in which the acetic or propionic acid solution of the chenodeoxycholic acid salt is diluted by the addition of water.

7. A process as claimed in claim 1, in which the acetic or propionic acid solution of the chenodeoxycholic acid salt is diluted by pouring said solution into water.

8. A process for the purification of crude chenodeoxycholic acid which comprises forming a mixture of methanol, the crude acid, a base and a calcium salt, whereby the crystalline calcium salt of chenodeoxycholic acid is precipitated, separating the salt, dissolving it in a solution of acetic acid, diluting this solution with water to precipitate the free acid in purified form, and recovering the purified acid.

9. A process for preparing the high melting point form of chenodeoxycholic acid (as herein defined) which comprises the steps of preparing an aqueous suspension of chenodeoxycholic acid of the low melting form (as herein defined) or amorphous form (as herein defined), seeding said aqueous suspension with preprepared cyrstalline high melting point chenodeoxycholic acid and treating the chenodeoxycholic acid product, in suspension, at a temperature of not greater than 85° C to effect substantially complete conversion of the solid acid to the high melting point form.

10. A process as claimed in claim 9, in which the chenodeoxycholic acid of the low melting form is obtained by subjecting crude chenodeoxycholic acid to a purification process comprising the steps of forming a mixture of methanol, the crude acid, a base and a calcium or strontium salt, whereby the crystalline calcium or strontium salt of the chenodeoxycholic acid is precipitated, separating the salt, treating the separated salt with an acidic reagent and isolating purified chenodeoxycholic acid.

11. A process as claimed in claim 9, wherein the chenodeoxycholic acid of low melting or amorphous form is obtained by the process of claim 1.

12. A process as claimed in claim 9, wherein the preprepared crystalline high melting point chenodeoxycholic acid used for seeding said aqueous suspension of the acid is obtained by dissolving chenodeoxycholic acid of the low melting or amorphous forms in dilute sodium hydroxide, adding hydrochloric acid until the pH of the solution is brought down to approximately 1 to precipitate the chenodeoxycholic acid, isolating the precipitated material and drying it until a dry powder product is obtained.

13. A process as claimed in claim 12, wherein the precipitated material is collected on a sintered glass funnel, washed with water, dried in a vacuum oven at 75° C and 50 torr for 15 minutes, the fused material broken up and the product dried for 2 hours at 75° C and 50 torr.

14. A process as claimed in claim 9, wherein the preprepared crystalline high melting point chenodeoxycholic acid used for seeding said aqueous suspension of the acid is obtained by heating chenodeoxycholic acid of the low melting or amorphous forms to 150° C in a melting point tube, at a very slow heating rate such that melting of the acid is avoided, keeping the product at this temperature for from 5 to 10 minutes and subsequently using it to seed a warm solution of low melting or amorphous chenodeoxycholic acid in acetonitrile thereby precipitating solid acid of the high melting point form.

15. A process as claimed in claim 9, wherein the treatment of the acid product to convert it substantially completely to acid of the high melting point form is effected by slowly warming a suspension of the solid acid to a temperature of not more than 85° C.

16. A process as claimed in claim 15, wherein the suspension of the solid acid is heated to a temperature of from 65° to 80° C.

17. A process as claimed in claim 10, wherein the treatment of the acid product to convert it substantially completely to acid of the high melting point form is effected by slowly warming a suspension of the solid acid to a temperature of not more than 85° C.

18. A process for preparing the high melting point form of chenodeoxycholic acid (as herein defined) which comprises preparing an aqueous suspension of chenodeoxycholic acid of the low melting and/or amorphous form (as herein defined) prepared according to the process of claim 1, seeding said aqueous suspension with pre-prepared crystalline high melting point chenodeoxycholic acid and slowly warming said seeded suspension of the solid acid to a temperature of not more than 85° C to convert the acid substantially completely to the high melting point form.

19. A process as claimed in claim 9, wherein the treatment of the solid acid to convert it substantially completely to acid of the high melting point form is effected by subjecting a suspension of the solid acid to ultrasonic vibration while maintaining the temperature at or below 85° C by cooling the suspension.

20. A process as claimed in claim 9, wherein the aqueous acetic acid solution of the chenodeoxycholic acid is poured into water to precipitate the free acid and the seeding of the suspension therein is carried out simultaneously by means of suspending preprepared crystalline high melting-point chenodeoxycholic acid in said water prior to the addition of the aqueous acetic acid solution.

21. A process for the preparation of pure chenodeoxycholic acid of the high melting point form (as herein defined) which comprises preparing the crystalline calcium salt of chenodeoxycholic acid of the low melting form (as herein defined) or amorphous form (as herein defined) by forming a mixture of methanol, the crude acid, a base and a calcium salt, whereby the crystalline calcium salt of chenodeoxycholic acid is precipitated, separating the salt, taking up the crystalline calcium salt in aqueous acetic acid to form a solution of the free chenodeoxycholic acid, diluting said solution with water to form a suspension of the acid and seeding the suspension with pure chenodeoxycholic acid of the high melting point form (as herein defined), isolating the product formed, washing it, resuspending the solid product in water and heating this suspension of chenodeoxycholic acid in water slowly to a temperature of not greater than 85° C to convert the acid substantially completely to the high melting point form.

22. A process as claimed in claim 21, wherein the aqueous acetic acid solution of the chenodeoxycholic acid is poured into water to precipitate the free acid and the seeding of the suspension therein is carried out simultaneously by means of suspending preprepared crystalline high melting-point chenodeoxycholic acid in said water prior to the addition of the aqueous acetic acid solution.

23. A process as claimed in claim 9, and further including the steps of filtering off the converted high melting point form of chenodeoxycholic acid and drying the solid acid to give the final product.

24. A process as claimed in claim 18 and further including the steps of filtering off the converted high melting point form of chenodeoxycholic acid and drying the solid acid to give the final product.

25. A process as claimed in claim 21, and further including the steps of filtering off the converted high melting point form of chenodeoxycholic acid and drying the solid acid to give the final product.

* * * * *